United States Patent

Maniglia

[11] Patent Number: 5,906,635
[45] Date of Patent: May 25, 1999

[54] ELECTROMAGNETIC IMPLANTABLE HEARING DEVICE FOR IMPROVEMENT OF PARTIAL AND TOTAL SENSORYNEURAL HEARING LOSS

[76] Inventor: Anthony J. Maniglia, 14450 County Line Rd., Hunting Valley, Ohio 44022

[21] Appl. No.: 08/912,710

[22] Filed: Aug. 18, 1997

Related U.S. Application Data

[60] Division of application No. 08/629,540, Apr. 9, 1996, abandoned, which is a continuation-in-part of application No. 08/376,750, Jan. 23, 1995, Pat. No. 5,558,618.

[51] Int. Cl.$^6$ .................................................. H04R 25/00
[52] U.S. Cl. ............................................................... 607/57
[58] Field of Search ................................. 600/25; 607/57

[56] References Cited

U.S. PATENT DOCUMENTS

| | | | |
|---|---|---|---|
| 3,870,832 | 3/1975 | Fredrickson | 600/25 |
| 5,015,224 | 5/1991 | Maniglia | 600/25 |
| 5,558,618 | 9/1996 | Maniglia | 600/25 |

OTHER PUBLICATIONS

Maniglia et al. "A Contactless Electromagnetic Implantable Middle Ear Device for Sensorineural Hearing Loss", ENT Journal, pp. 78–90, Feb. 1994.

*Primary Examiner*—Scott M. Getzow
*Attorney, Agent, or Firm*—Vytas R. Matas

[57] ABSTRACT

A partially implantable hearing device for improvement of partial and total hearing loss has a high coercivity post type permanent target magnet mounted to the ossicular chain by METABOND adhesive and being driven by a cylidrically shaped air core driving coil extending around the post magnet in a contactless manner. The drive coil responds to auditory vibrations sensed by an externally concealed unit which converts these signals to an electrical signal transmitted to an externally located antenna which transmits same to an internally mounted antenna electronically connected to the air core electromagnetic driving coil to improve partial hearing loss. For total hearing loss restoration, a speech processing unit is mounted inside the mastoid cavity having a intracochlear electrode which is inserted into the cochlea through the oval window to reach the nerve endings thereof and transmit speech signals capable of being understood by the brain. For total hearing loss a totally implantable system with a non rechargeable or rechargeable battery, receiving antenna for remote control of on/off switch, volume, speech processor and programing is used with a biologic-electronic microphone activated by the implanted rechargeable battery to interact with implanted electronics for transmission of electrical signal directly to the cochlear nerve endings.

15 Claims, 12 Drawing Sheets

ELECTROMAGNETIC IMPLANTABLE HEARING DEVICE FOR IMPROVEMENT OF PARTIAL AND TOTAL SENSORYNEURAL HEARING LOSS

This application is a division of application Ser. No. 08/629,540, filed Apr. 9, 1996, now abandoned. Which is a continuation in part of application Ser. No. 08/376,750 filed Jan. 23, 1995 now U.S. Pat. No. 5,558,618 issued Sep. 24, 1996.

BACKGROUND OF THE INVENTION

1. Field of the Invention

The present invention relates to partially implantable hearing devices generally and particularly to such devices which use electromagnetic drivers and target permanent magnets to stimulate the ossicular chain of the middle ear for restoring partial hearing loss and for totally implantable devices which stimulate the cochlear nerve endings to restore total hearing loss.

2. Description of the Prior Art

Conventional prior art hearing aids are composed of a microphone, an amplifier, a battery as a power source, and a speaker or earphone (commonly referred to as a receiver in the hearing aid industry). Known implantable hearing device have the same basic components, except that the speaker is replaced by a driving vibrating component, such as an electromagnetic coil or a piezoelectric system of biomorph design. Environmental sound energy, as it passes through either device, is converted by the microphone into an electrical signal which is routed to an amplifier. In the conventional hearing aid, the speaker converts the amplified electrical signals into acoustic energy, which is then transmitted to the tympanic membrane and ossicular chain. In the implantable middle ear hearing device, the speaker is eliminated, being replaced by the vibratory component which drives the ossicular chain.

Partially implantable middle ear hearing devices are also known. These devices have a small, lightweight high coercivity magnet effectively glued to the ossicular chain by a bio compatible bonding material such as METABOND or SUPERBOND adhesives manufactured in the USA and Japan respectively. The magnet is driven by an air core electromagnetic coil optimally spaced from the target magnet at a distance of approximately 1 mm. There is no contact between the air core coil and the target magnet.

These devices have an external unit and an internal unit. The external unit receives, amplifies, and transmits sound energy as radio frequency signals. The external unit consists of a microphone, a radio frequency (RF) amplifier, a transmitting antenna, and a battery. Using existing microchip technology, these components are miniaturized to a unit with dimensions of 10×10×5 mm without the battery. This allows the small external unit to be effectively concealed in a post auricular skin pocket and easily placed and removed by the patient. The skin pocket functions to maintain the external and internal antennae in proper proximity and alignment for optimal RF signal transmission. Leaving the pocket open superiorly and partially open inferiorly allows the area to remain accessible to hygienic maintenance. Dehydrating agents such as alcohol may be easily applied with a cotton-tipped applicator, and the pocket may be dried with a hair dryer after regular showers and shampoos.

The internal unit consists of a receiving antenna, a titanium support, implanted electronics, an electromagnetic (EM) transducer (driving coil), and the high coercivity magnet. The electronics (diode and capacitor), driving coil, and magnet are hermetically sealed in a helium filled laser-welded titanium case. A glass-insulated feedthrough attaches the electronics to silicone or polytetrafluoroethylene-coated platinum iridium or stainless steel wires of the receiving antenna. The precise alignment of the transmitting (external) and receiving (internal) antennae permits transcutaneous transfer of the sigma delta modulated radio frequency signal (8 to 10 $MH_z$). The implanted electronics function to receive the radio frequency signal that has been processed by the external electronics and to transform this energy into an audio frequency input to the driving coil. The driving coil in turn creates a magnetic field, which activates the target magnet attached to the body of the incus. Through the ossicular chain, the vibrations are transmitted to the inner ear fluids, activating the organ of Corti.

The magnet used is a neodymium-iron-boron (NdFeB) permanent magnet of great coercive force and high flux density. The magnet, weighs 8.0 mg, is hermetically sealed in a laser-welded 6-mg titanium case containing a helium atmosphere. Two of such magnets are used, stacked on top of each other. On the basis of fresh human cadaver studies, the magnet-titanium assembly weight load of 65 mg and 110 mg has a negligible effect at the malleus and incus, respectively, on the frequency response.

The external electronics associated with the transducer are designed to apply only push forces on the magnet-incus assembly. An air-core coil placed in the attic of the middle ear is used because it does not exert a constant bias force on the ossicular chain. If the system is idling, there is no steady force applied to the incus-magnet assembly. In order to determine the size of the driving coil, 20 preserved human cadaver temporal bones were microsurgically dissected. Measurements were made of the mastoid cavity, antrum, attic, and body of the incus. Owing to the anatomic characteristics of the attic, the outside diameter of the driving coil assembled in a titanium case was limited to 5.0 to 6.0 mm. outside diameter. Initially, an efficient coil was built with a 3.0-mm outside diameter, 0.75-mm inside diameter, and a length of 1.0 mm, composed of 2200 turns of 52 AWG copper wire with 600 ohms resistance. A more efficient coil with 2668 turns of 52 AWG copper wire with 875 ohms resistant was later built for short-and long-term animal experimentation. Computer simulations were instrumental in the selection of this coil design. For the human device a coil with 3800 turns and a resistance of 1415 ohms is preferably used. This coil has been tested experimentally and found to generate 76% more force when compared to the 2668 turn coil.

These described devices while operating to provide restoration of partial hearing loss did not have any means to activate the cochlear nerve endings in patients who had total hearing loss due to a malfunctioning cochlea. Also, these devices had no provision for adjusting the device to accommodate growth of the patient over the years which is a problem especially prevalent in implants for growing children.

BRIEF SUMMARY OF THE INVENTION

The present invention solves the problems associated with the mentioned prior art devices as well as other problems by providing an electromagnetic partially implantable hearing restoration device for partial and total hearing loss restoration which also has adjustability to accommodate changes caused by the growth of young patients receiving such an implant while young.

To accomplish this, a titanium encased hermetically sealed post type permanent magnet is bonded to the ossicular chain (body of the incus or anvil) having a cylindrical electromagnet located around the post a predetermined distance therefrom. The electromagnet responds to signals from a microphone and antenna with modulating circuits to establish radio frequency signals to the electromagnet to actuate the ossicular chain and improve hearing thereby.

In cases of total hearing loss, a programing and speech processor are mounted inside the drilled out mastoid bone which is responsive to the actuations of the ossicular chain to establish signals along an intracochlear electrode located in the cochlea near the nerve endings thereof which are intelligible to the brain when they are transmitted to the brain by these nerve endings.

In view of the foregoing it will be seen that one aspect of the present invention is to provide a partially implantable electromagnetic hearing device to restore partial hearing loss.

Another aspect of the present invention is to provide a totally implantable electromagnetic hearing device to improve hearing loss due to a non functioning cochlea.

Yet another aspect of the present invention is to provide a partially implantable hearing restoration device which has adjustment for growth of a young patient receiving the implant at an early age.

These and other aspects of the present invention will be more fully understood after reviewing the following description of the preferred embodiment when considered with the appended drawings.

DETAILED DESCRIPTION OF THE PREFERRED EMBODIMENT

Figure 1:
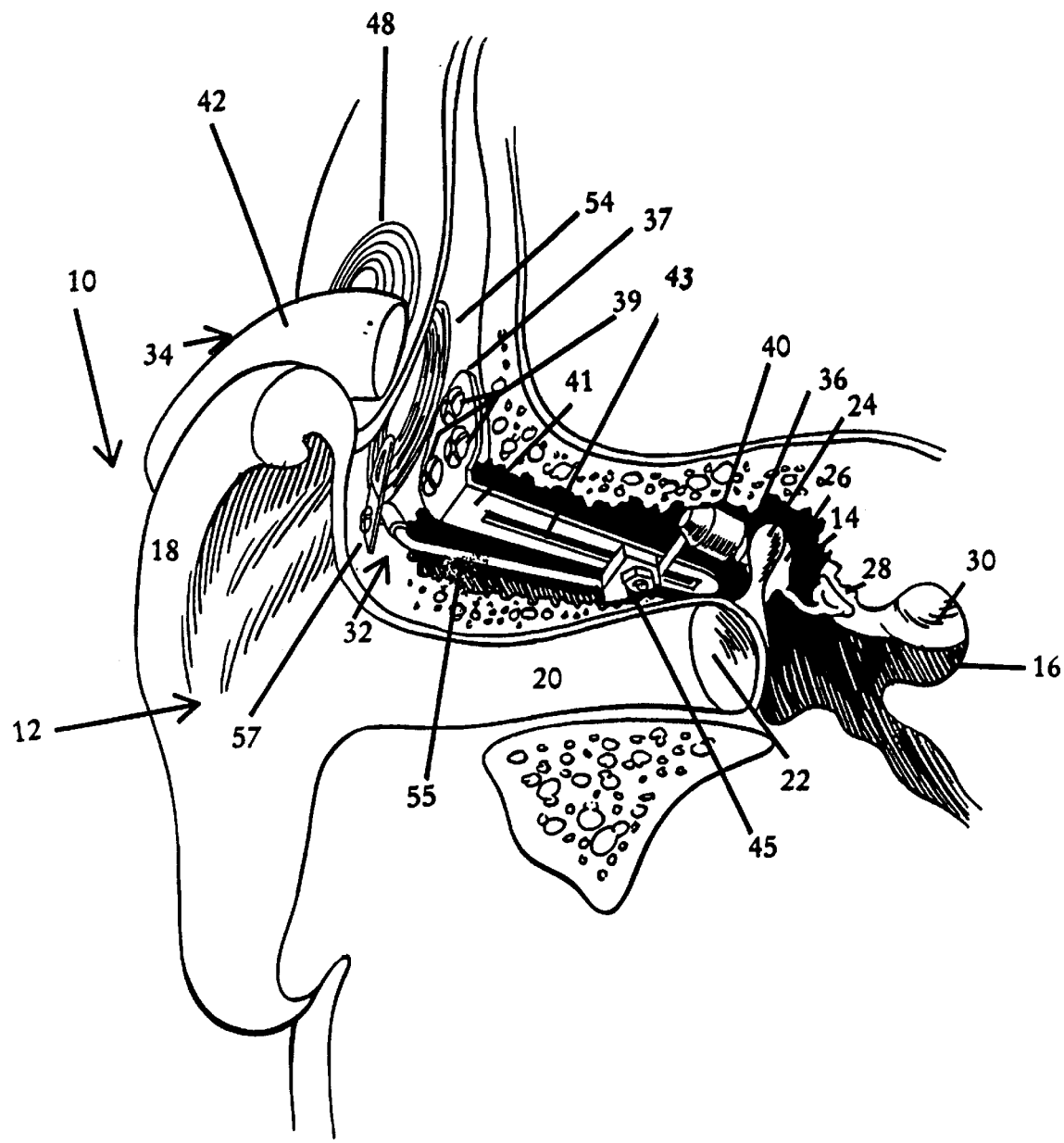
FIG. 1. is a depiction of a human ear having the partially implantable hearing restoration device internal unit of the present invention shown mounted therein for restoration of partial hearing loss.
Figure 2:
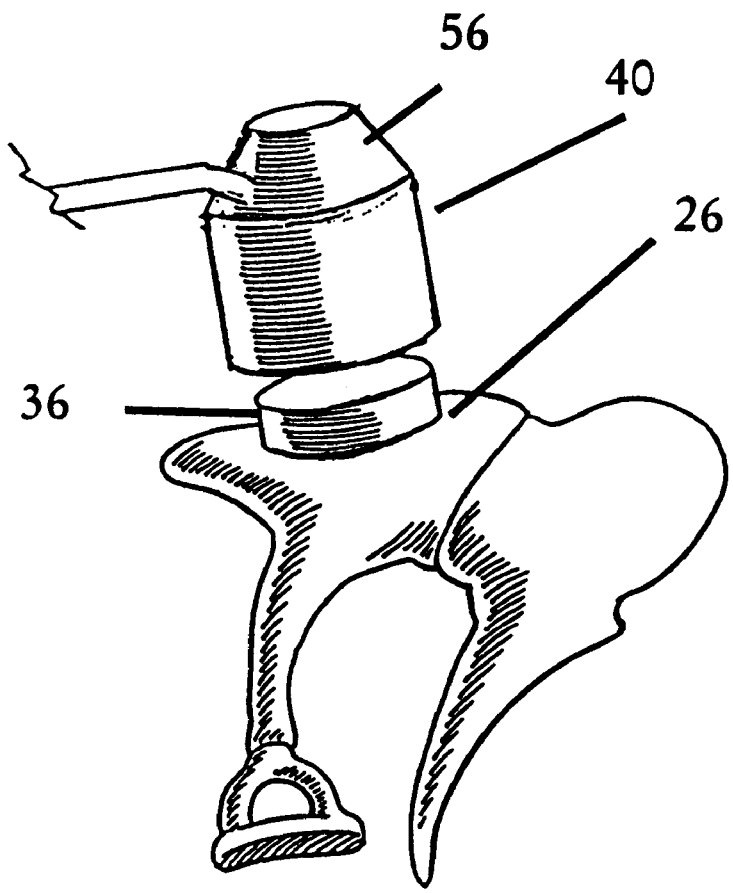
FIG. 2 is an expanded view of the electromagnet and permanent magnet locations in the FIG. 1 depiction.

Referring now to the drawings generally, wherein like numerals designate the same element throughout the several drawings, and to FIGS. 1. through 4 in particular, there are shown cross-sectional views of an ear, generally referred to as 10, which has received a partially implantable hearing device of the present invention.

The ear 10 is made up of an outer ear 12, a middle ear 14, and an inner ear 16. The outer ear 12 includes an auricle or pinna 18, and an outer ear canal 20. The pinna 18 collects acoustic energy or sound waves from the environment and directs them into the outer ear canal 20 which conveys the sound waves by air conduction to a tympanic membrane or ear drum 22, which separates the outer ear 12 from the middle ear 14.

The middle ear 14 contains a series of three tiny interconnected bones; the malleus (hammer) 24; the incus (anvil) 26; and the stapes (stirrup) 28. Collectively, these three bones are known as the ossicles or the ossicular chain. The malleus 24 is attached to the tympanic membrane 22 while the stapes 28, the last bone in the ossicular chain, is attached to the oval window of the inner ear (not shown).

Sound waves that travel down the outer ear canal 20, strike the tympanic membrane 22 and cause it to vibrate. The malleus 24, being connected to the tympanic membrane 22, is thus also set into motion, along with the incus 26 and the stapes 28. These three bones in the ossicular chain act as a set of levers to amplify the tiny vibrations received by the tympanic membrane 22. By the time the vibrations are transmitted to the oval window (not shown) the pressure vibrations received by the tympanic membrane 22 have been magnified by as much as 22 times. The stapes vibrates in turn, causing fluid in a spiral structure known as the cochlea 30 to move along its length. Very small hairlike cells or nerve endings (not shown) in the cochlea 30 are stimulated by the movement of fluid in the cochlea 30. There, hydraulic pressure displaces the inner ear fluid and mechanical energy in the hair cells is transformed into electrical impulses which are transmitted to neural pathways and the hearing center of the brain (temporal lobe), resulting in the perception of sound.

A first embodiment of the present invention is drawn to an external unit 34, which will be described later, and an internal implantable hearing device generally referred to as internal unit or assembly 32. The internal assembly 32 includes an implanted unit having a high coercivity permanent magnet assembly 36 bonded to the incus 24 of the ossicular chain and a supporting structure 38 having a horizontal support 37 which is screwed into the internal ear by three screws 39 from which a vertical strip 41 extends at a right angle. The vertical strip 41 has a cut out portion 43 formed therein along which a lock assembly 45 is moved and locked in place to position an air core electromagnetic coil 40 spaced approximately 0.5 to 1 mm. away from the permanent magnet assembly 36.

Figures 11, 12:
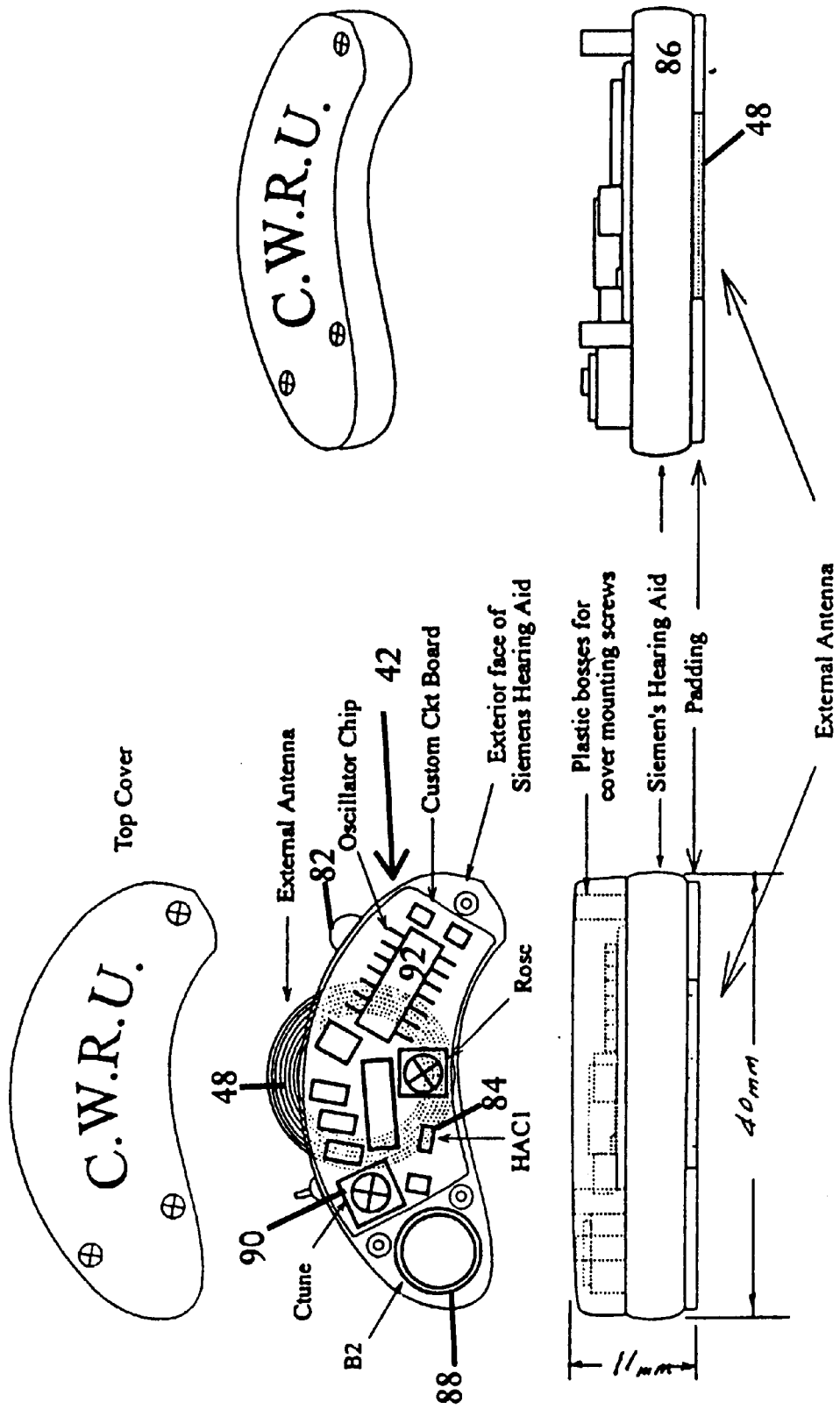
FIG. 11. is a physical depiction of the external unit of FIG. 10.
FIG. 12. is a side view of the FIG. 11 unit.
Figure 13:
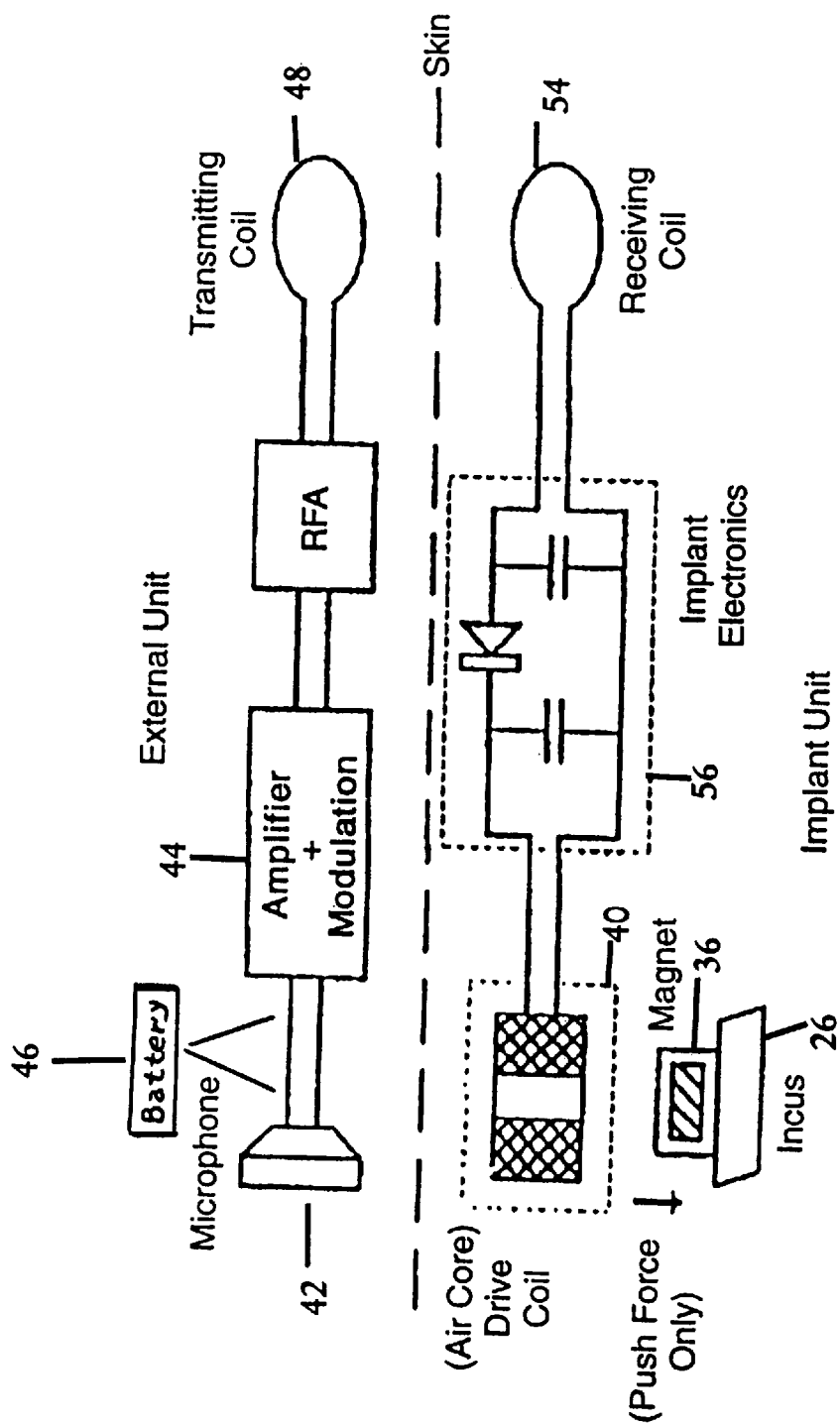
FIG. 13. is a schematic of the relationship between the external and internal units of the present invention.

As may be best seen with additional reference to FIG. 12, the external unit 34 is adapted to be located externally and medially to an upper portion of the pinna 18. The external unit 34 includes a microphone or 42, an amplifier 44, a power supply battery 44 and 46, not seen here but located inside the case of unit 34, and an external antenna 48. Since the external unit 34 is not inserted into the outer ear canal, it need not be encased and hermetically sealed in a silicone mold as would be required for an implanted unit. The unit 34 may be miniaturized and designed to be semi-implantable and the external unit well concealed in the postauricular area in a skin pocket hidden by the auricle. Such implanting is described in detail in U.S. Pat. Nos. 4,957,478 and 5,015,224. The reader is referred thereto for an explanation of the procedure and benefits of such concealed semi-implantations. An important advantage of the present design is that the air canal 20 is not plugged by any device that could very well cause irritation, infection, discomfort, or accumulation of wax. The ear canal is wide open, maintaining its normal anatomy and physiology without attenuation of sound or occlusion effect.

The external unit 34 receives, amplifies, and transmits sound energy as radio frequency signals. Using existing micro chip technology, the microphone 42, amplifier 44, battery 46 and antenna 48 can be miniaturized to a unit with dimensions of 10×10×5 mm without the battery. This small external unit can be effectively concealed in a postauricular skin pocket and is easily placed and removed by the patient. The skin pocket 50 functions to maintain the external antenna 48 and internal antenna 54, in proper proximity and alignment for optimal RF signal transmission. Leaving the pocket open superiorly and partially open inferiorly allows the area to remain accessible to hygienic maintenance. Dehydrating agents such as alcohol may be easily applied with a cotton-tipped applicator, and dried with a hair dryer after regular showers and shampoos.

The internal unit 32 consists of receiving antenna 54 which leads through a titanium shaft 55 supported near the internal antenna 54 by a retaining assembly 57. The internal antenna is approximately 14 mm wide and comprises approximately 12 loops which terminate at the retaining assembly 37 where it is grounded and from which it is connected to a wire glass sealed in the titanium shaft 55 which acts as a feedthrough ending in a connection to the implanted electronics 56. The internal electronics comprise an electromagnetic (EM) transducer (driving coil), 40 and the target magnet 36. The electronics, driving coil, and target magnet are all hermetical sealed in laser-welded titanium cases. A glass-insulated Platinum feedthrough post attaches by laser welding the electronics to a silicon or polytetrafluoroethlene-coated platinum iridium or stainless steel wires of the receiving antenna 54. The precise alignment of the transmitting 48 and receiving 54 antennae, permits transcutaneous transfer of the sigma delta modulated radio frequency signal (8 to 10 $MH_z$). The implanted electronics function to receive the radio frequency signal that has been processed by the external electronics and to transform this energy into an audio frequency field as input to the driving coil. The driving coil in turn creates a magnetic field, which activates the target magnet attached to the body of the incus. Through the ossicular chain, the vibrations are transmitted to the inner ear fluids, activating the organ of Corti.

A neodymium-iron-boron (NdFeB) target permanent magnet 36 is used because of its great coercive force and higher flux density. The target magnet is hermetically sealed in a laser-welded titanium case containing a helium atmosphere to prevent corrosion of the magnet. This assembly weighs approximately 29 mg. On the basis of fresh human cadaver studies it was found that the magnet-titanium assembly weight load of 65 mg. and 110 mg. has a negligible effect at the malleus and incus, respectively, on the frequency response. Experiments with cats have shown that two magnets encased in Titanium (28 mg.) cause a hearing loss of only 5 db. SPL. A mastoipectomy (antrotomy) and atticotomy are performed, and the NdFeB titanium encased magnet is cemented to the incus. NdFeB is a permanent magnet with a coercive force (Hc) of 10.6 KOe as compared with samarium cobalt (SmCo5) which has an Hc of 7.5 KOe. Also, NdFeB has higher flux density (Br) per unit density. (NdFeB=1.86 KGauss: SmCo5=0.665 KGauss) and it has better machining properties. If not properly hermetically sealed, the iron will oxidize and the magnet will lose its strength. However, our NdFeB titanium-encapsulated magnet 36 is laser welded and hermetically sealed in a titanium case with a helium atmosphere. The titanium case can also be cemented in the incus with a post introduced in a hole created by a KTP laser or cemented on the incus body after light etching of the bone (titanium case with no post). A combination of both methods is also feasible. As was mentioned, the easiest, most efficient, and non invasive way is just to cement it to the body of the incus. The diameter of the encapsulated magnet is the same size as the width of the incus. Titanium is an excellent lightweight nonmagnetic bio compatible material, and it should not affect the viability of the incus. Another magnet can be stacked or cemented to the permanently fixed magnet in the incus with negligible reduction of tympanic membrane vibration.

One of the problems in mounting the magnet 36 to the incus was how to secure the titanium-encapsulated magnet without mechanically drilling into the incus. We experimented with micro drilling as well as the use of KTP and $Co_2$ lasers to create cavities that would allow a titanium post attached to the case of the magnet to be biointegrated into the body of the incus. We found that these techniques were very invasive and rather destructive. Further, they did not permit the tight mechanical fit into the drilled incus cavity required for the proper positioning of the magnet until the eventual osseus bio integration of the titanium post. This technique was not successful even when a spring was attached to the post to secure proper positioning in the incus cavity.

An efficient, biocompatible, adhesive type of cement was the best way to affix the titanium-magnet assembly on the body of the incus. There being no such adhesive available for otologic use, I turned my attention to the dentistry literature in order to select a suitable cement that would satisfy my needs. A titanium-bone cement (METABOND) was found to properly secure the magnet to the incus. METABOND is the USA brand name for an adhesive of multiple compounds developed in Japan by Sun Medical Co. of Kyoto Japan where it is known as SUPERBOND. This adhesive is approved by the U.S. Food and Drug Administration (FDA) as a Class II dental device, #K900303, for cementing titanium to dentine; it has been subjected to previous bio compatibility studies applicable to dentistry. Further research was then done by us to test the tensile strength and resistance to shearing force and torque, using the rabbit as the animal model. Titanium disks were cemented with METABOND on the tibia of the rabbits after the tibia was etched with citric acid. Experiments in the rabbit after 3 months of implantation have shown excellent results. Our conclusion was that METABOND was most effective and least invasive for binding titanium to bone. The results of chronic experiments in cats demonstrated that METABOND would provide a very effective and long-lasting method of cementing the titanium magnet 36 to the incus after it was etched with citric acid. The average survival rate of these animals was 9.6 months.

The implant electronics 56 associated with the electromagnetic transducer 40 are designed to apply only push forces on the magnet-incus assembly. Two types of driving coils or electromagnetic transducers were considered; air core and soft magnetic core. The air-core coil was found superior because it does not exert a constant bias force on the ossicular chain. If the system is idling, there is no steady force applied to the incus-magnet assembly. In order to determine the size of the driving coil 40, 20 preserved human cadaver temporal bones were micro surgical dissected. Measurements were made of the mastoid cavity, antrum, attic, and body of the incus. Owing to the anatomic characteristics of the attic, the outside diameter of the driving coil assembled in a titanium case was limited to 5.0 to 6.0 mm. Initially, an efficient coil was built with a 3.0-mm outside diameter, 0.75-mm inside diameter, and a length of 1.0 mm, composed of 2200 turns of 52 AWG copper wire with 600 ohms resistance. Computer simulations were instrumental in the selection of this coil design.

Figure 7:
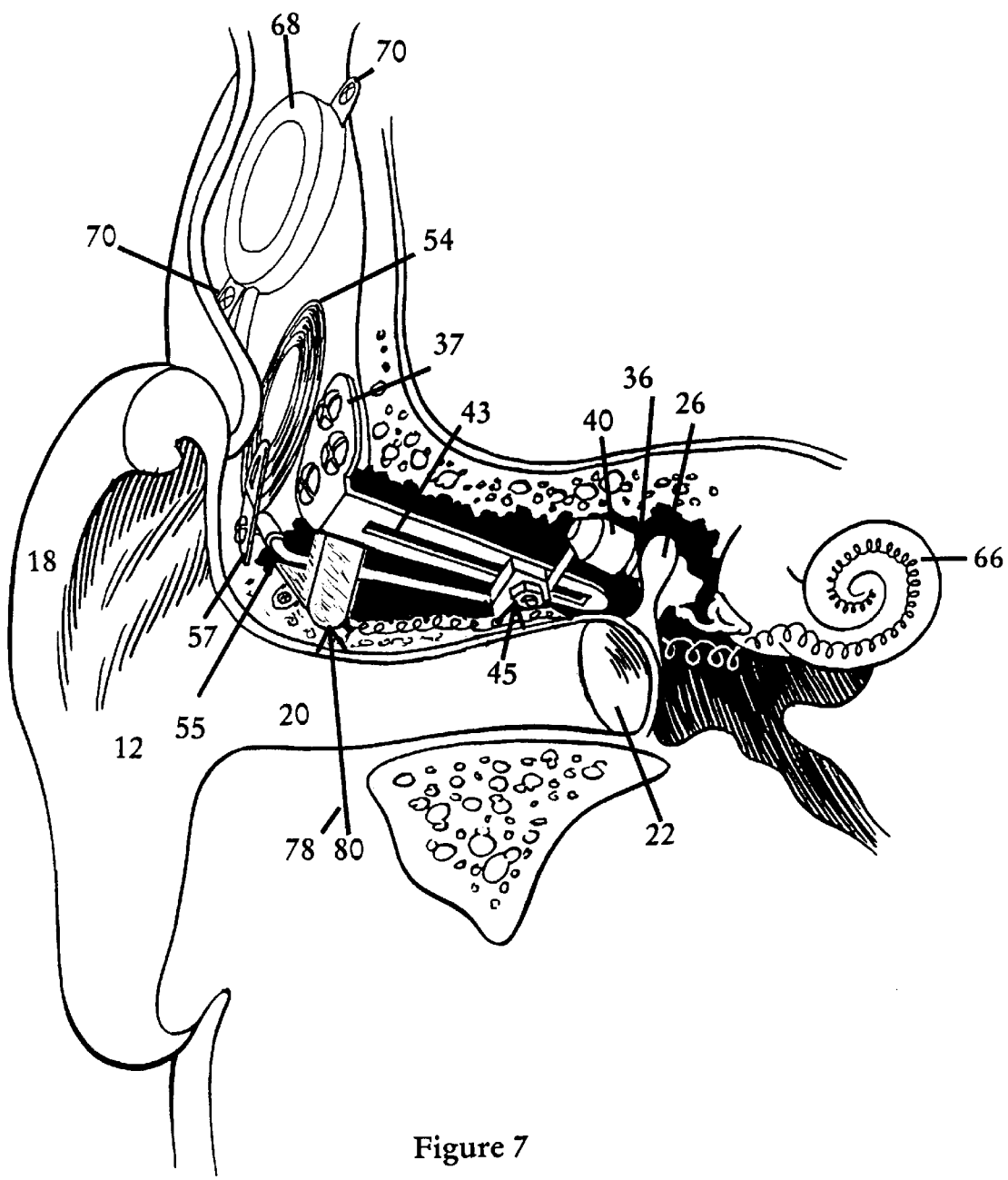
FIG. 7. is a depiction of a human ear having the partially implantable hearing restoration device internal unit of the present invention shown mounted therein for restoration of total hearing loss in adult patients.

Tests were performed to measure the effect of spatial relationships between the air coil 40 and the NdFeB magnet 36 in a set up best seen in FIG. 7. The DC force per mA was measured using an optical reflection-amplitude sensor 58 and a calibrated cantilevered glass strip 60 as a load cell. This device has a resolution of 0.05 um over a 5 $KH_z$ bandwidth with an accuracy of 10 percent. The NdFeB magnet 36 was affixed to one side of a 0.2 mm thick glass strip and a small mirror 62 was affixed to the opposite side. The air core coil 40 was placed at a known gap distance (d) from the face of the magnet 36 in addition the coil 40 was centered over the magnet. A current source 64 was used to drive the coil 40 and the displacement of the magnet/glass strip assembly was measured at varying gap distances, lateral displacements, and angular variations. With each 0.5 mm increase in gap distance (d), a 50 percent loss in force was noted. Loss in force was negligible for lateral displacements of ±0.5 mm. Force losses became significant at greater lateral distances. Angular variations up to 30° were not found to have a critical effect on the forces generated by the coil which drive the magnet. Experiments showed that no significant reduction of magnetic or frequency response occurred by the interposition of water, albumin, or serous otitis media glue material bridging the air space between the coil and the magnet attached to the incus. There is a steady force acting between the components due to surface tension of the glue from middle ear interfaced in the gap, more so at high frequency (10 $KH_z$). The gap d must be maintained at approximately 1 mm to prevent significant loss of signal from the electromagnet 40.

Figure 3:
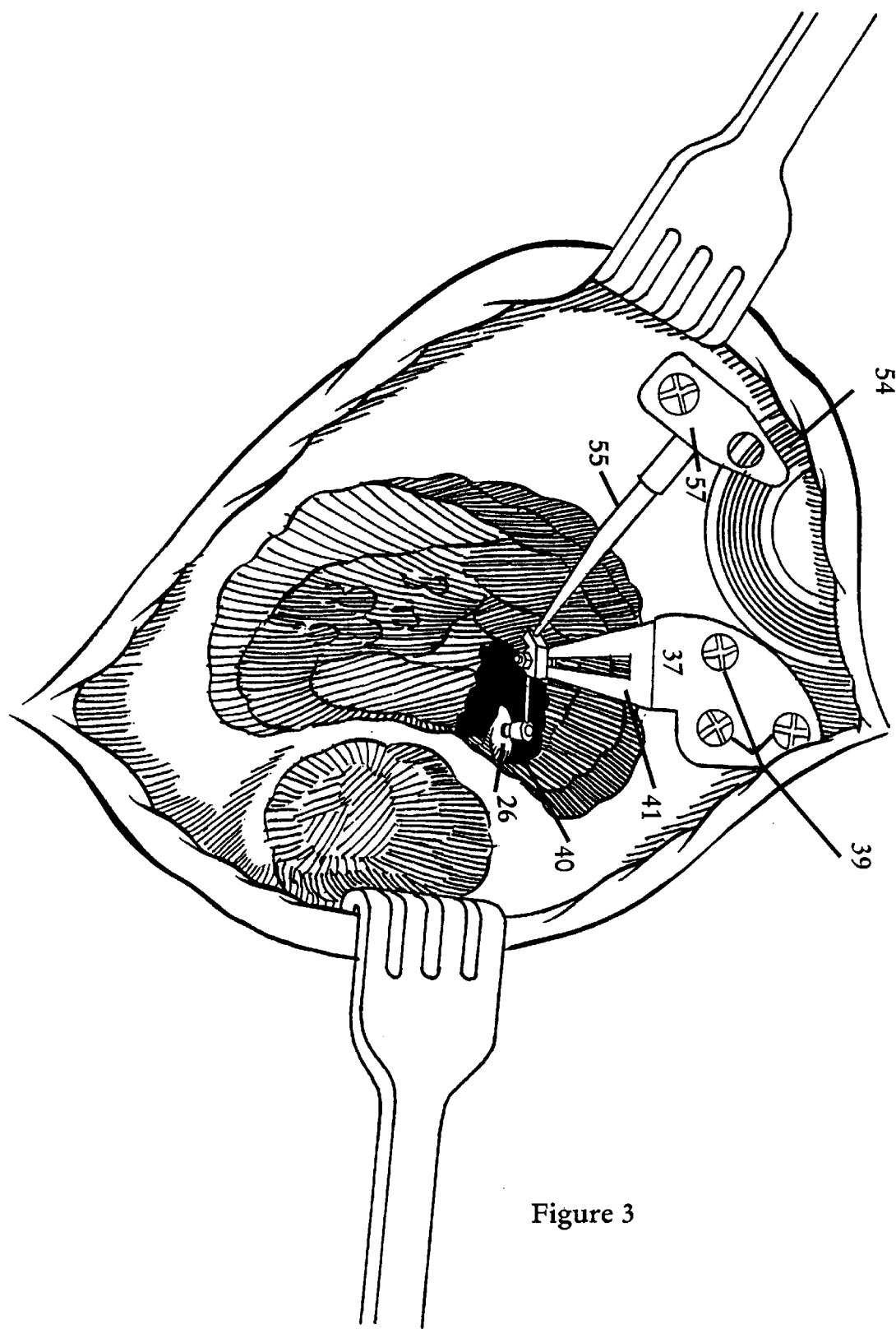
FIG. 3. is an expanded view of the support means and receiving antenna of the FIG. 1. depiction.
Figure 4:
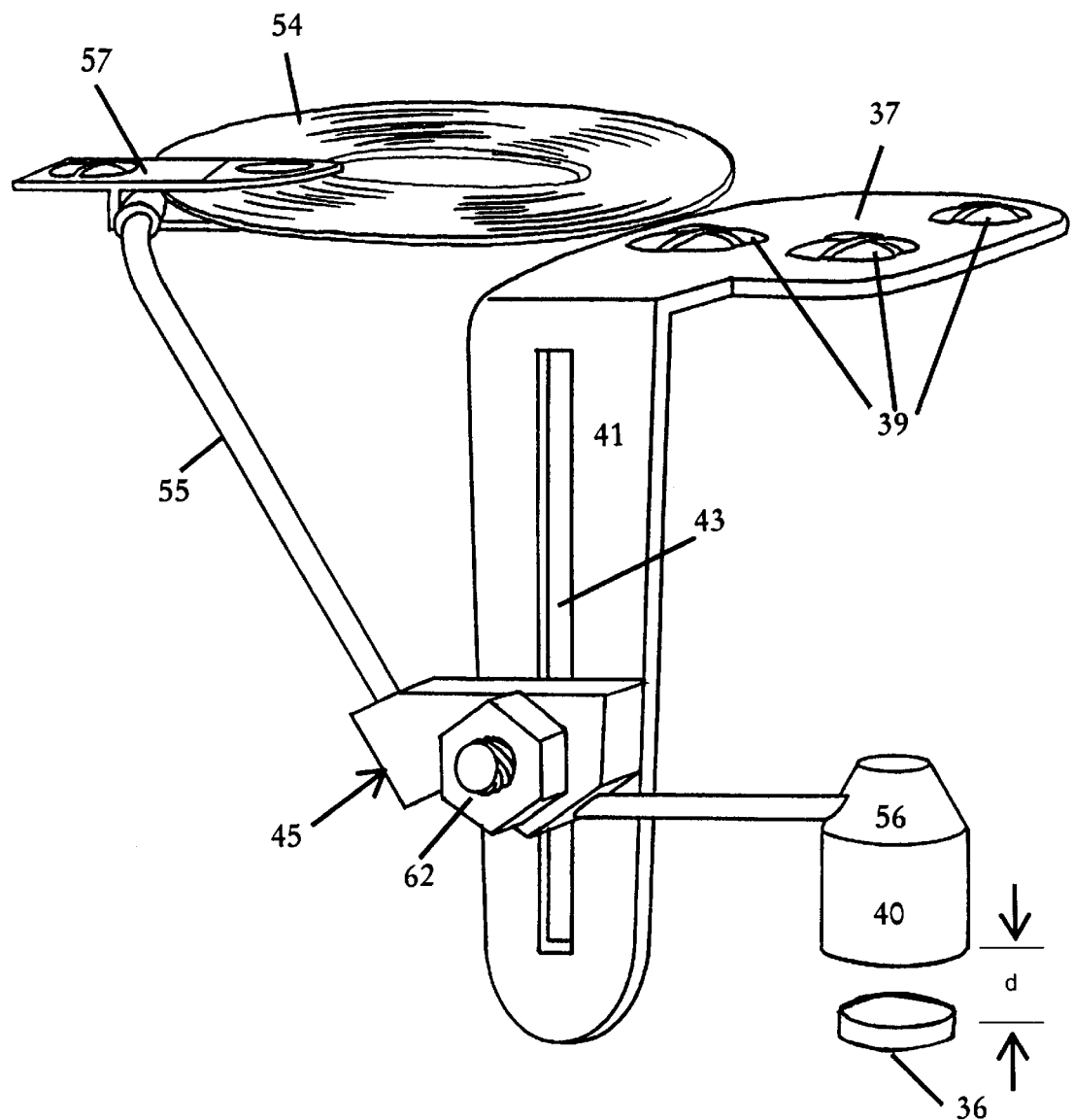
FIG. 4. is an expanded view of the support means of the FIG. 1 internal unit depiction.

To obtain this desired gap during the implanting of the internal assembly 32, the surgeon mounts the horizontal support of the assembly 37 to the temporal bone through screw fasteners 39 best seen in FIG. 3. The internal antenna 54 is retained by the support 57 in a bony niche in the area of the temporal bone which will align the internal antenna 54 with the external antenna 48 of the unit 34 when located in the niche to thus keep it from moving or breaking a wire of the antenna. As best seen in FIG. 4. the electronics case 56 is connected to an end of the rigid titanium tube 55 which is rigidly mounted to the locking assembly 45 to move up and down within the groove 43 in the vertical leg 41 of the assembly 34. The locking assembly is loosened or tightened to move or be locked in place in the groove 43 by a threaded screw 62 which extends into a nut (not shown) on the other side of the slot or groove 43 which is larger than the slot 43. When the assembly is loose, it is free to move up and down the slot 43. The surgeon moves the assembly 45 until the electromagnet 40, which is rigidly affixed to the case 56 and the Titanium shaft 55, rests against the permanent magnet 36. A template or other measuring device is then used to obtain the proper distance between the magnet 36 and the driving coil 40. The screw 62 is then tightened to assure that the 0.5 to 1 mm gap will be maintained.

Figure 5:
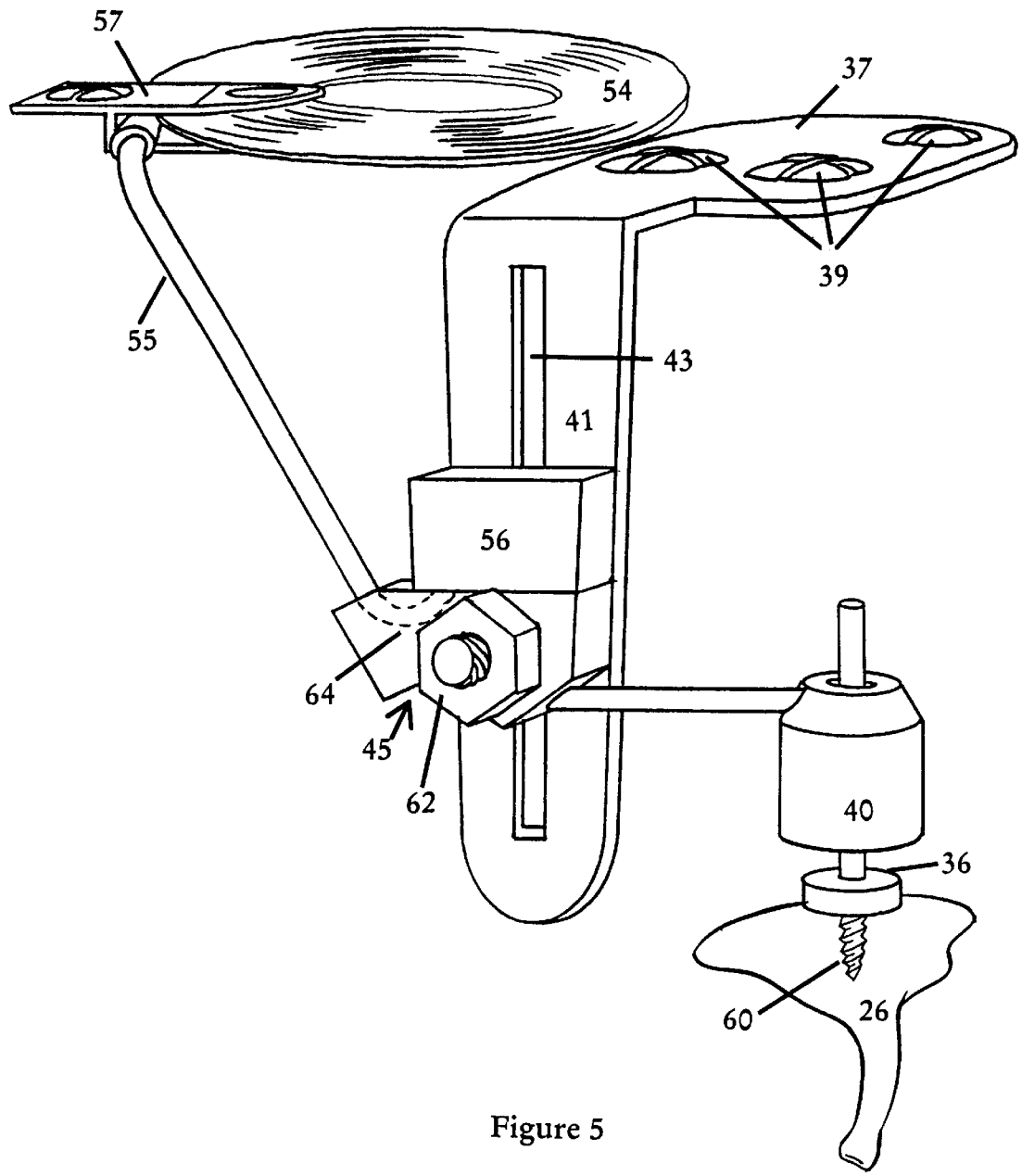
FIG. 5. is an expanded view of an alternate support means which may be used in the FIG. 1 internal unit depiction for growing patients.
Figure 6A:
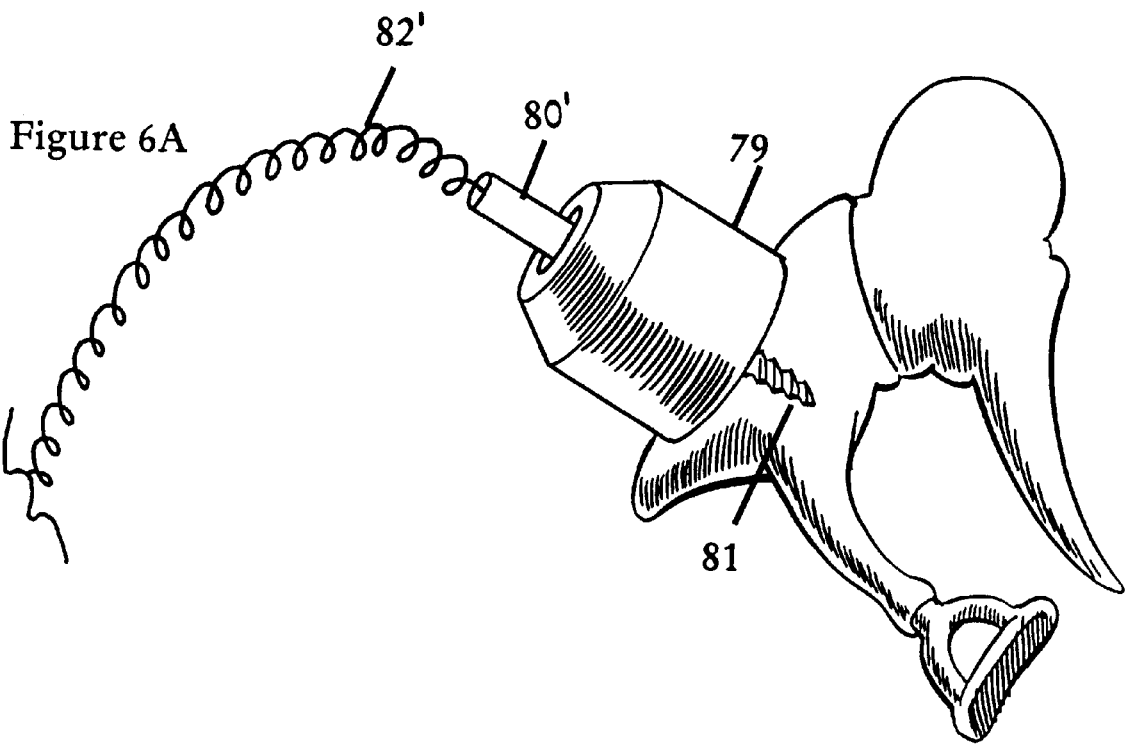
FIG. 6a. is another expanded view of the alternate design, applicable to both adults and children, of an electromagnet and magnet housed in a single titanium case connected by a wire to the electronics.
Figure 6:
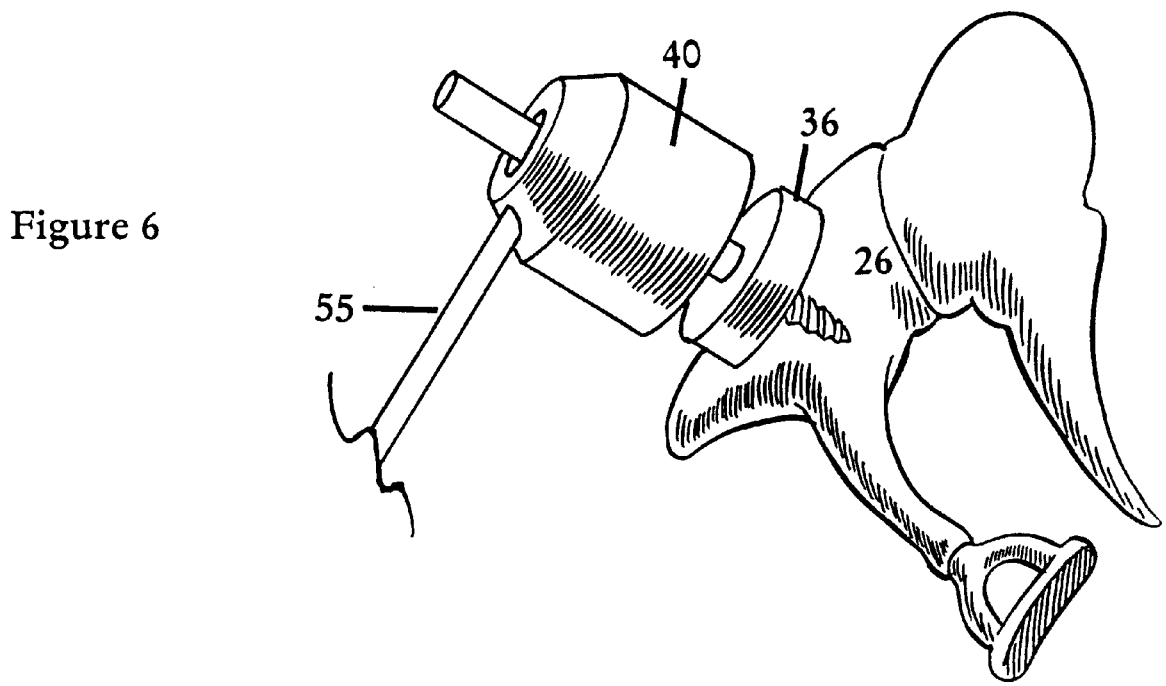
FIG. 6. is an expanded view of the alternate electromagnet and permanent magnet found in the FIG. 5 depiction.

Turning next to FIGS. 5–6, an alternate design for the partial hearing restoration device is described which is especially useful, for implants in growing children since the gap between the magnet and the drive coil of 3800 turns is maintained relatively constant over the growth of the child as the dimensions of his ear structure change due to the child's growth. The alternative design depicted on FIG. 6-A has a hermetically sealed Titanium encased drive coil and magnet. The magnet (Nd FeB) weights 8 mg and is maintained in a constant distance of 0.5 mg to the driving coil (2668 turns) by a spacer made out of soft silicone rubber to allow vibration contributed by inertia force. This assembly is secured to the incus with METABOND Cement. A post (81) attached to the case is cemented in a CO2 or KTP Laser made cavity located in the body of the incus The Titanium case has a glass insulated feedthrough 80 which is welded to a coiled wire 80 (silicone or Teflon) insulated which is connected to electronic box through another glass insulated feedthrough. The platinum iridium wire is coiled in a similar manner of these used for electrodes of muscle implants currently available commercially.

The changes involve the placement of the electronics 56, which were mounted to the driver 40, in an affixed position to the locking assembly 45. This new position of the electronics for demodulating the radio frequency is encased in a box 56' located on top of the assembly 45. The Titanium encased NdFeB magnet 36 is also changed to be formed as a post 36' which is inserted into a laser produced cavity in the body of the incus 26 and cemented therein by METABOND dental adhesive. The driver 40 is formed as a tubular member 40' extending angularly around the post 36' to have a gap of approximately 0.5 mm. The driver 40' has approximately 3800 turns of wire located within a hermetically sealed titanium hollow center air core. The electronics 56' are connected to the tubing 55 by a similarly formed connecting tube 62 which provides electrical communication between the driver 40' and the electronics 56'. The internal antenna 54 in a known manner.

It will now be seen that as the patients growth pattern causes a displacement of the post magnet 36' to the driver 40' this displacement is compensated by the length of the post 36' which extends through the driver 40'. The movement of the post 36' within the driver 40' thus still maintains the same gap and no deterioration in hearing results from such growth.

Turning next to FIGS. 7–12, a device for restoration of total hearing loss will be described for patients who are candidates for cochlear implant. Total hearing loss is due to the cochlea 66 of the inner ear being unable to transmit sound energy to the nerve endings therein which then in turn send sound and speech signals to the brain.

Figure 8:
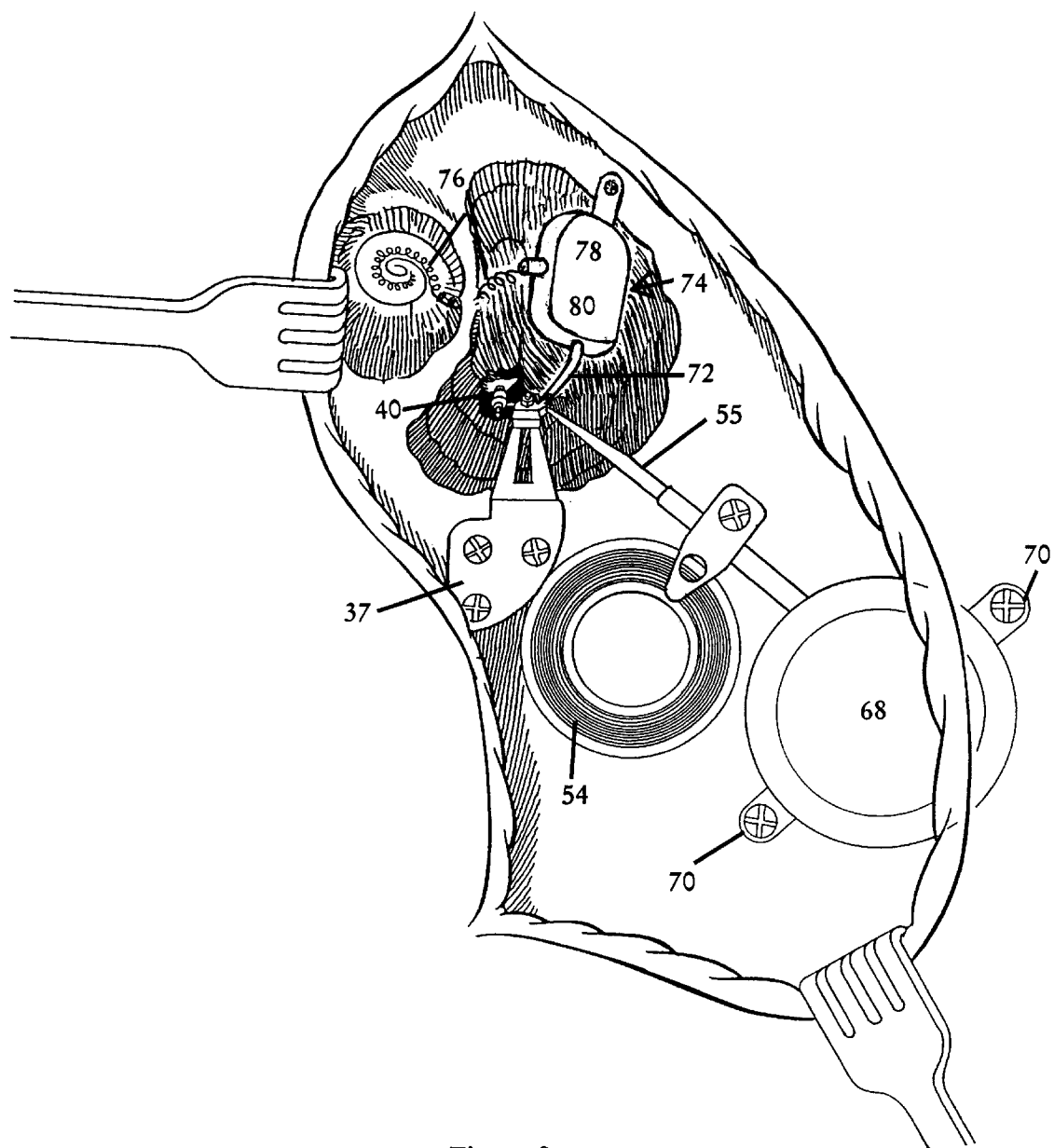
FIG. 8. is an expanded view of the support means and receiving antenna of the FIG. 7. depiction.
Figure 9:
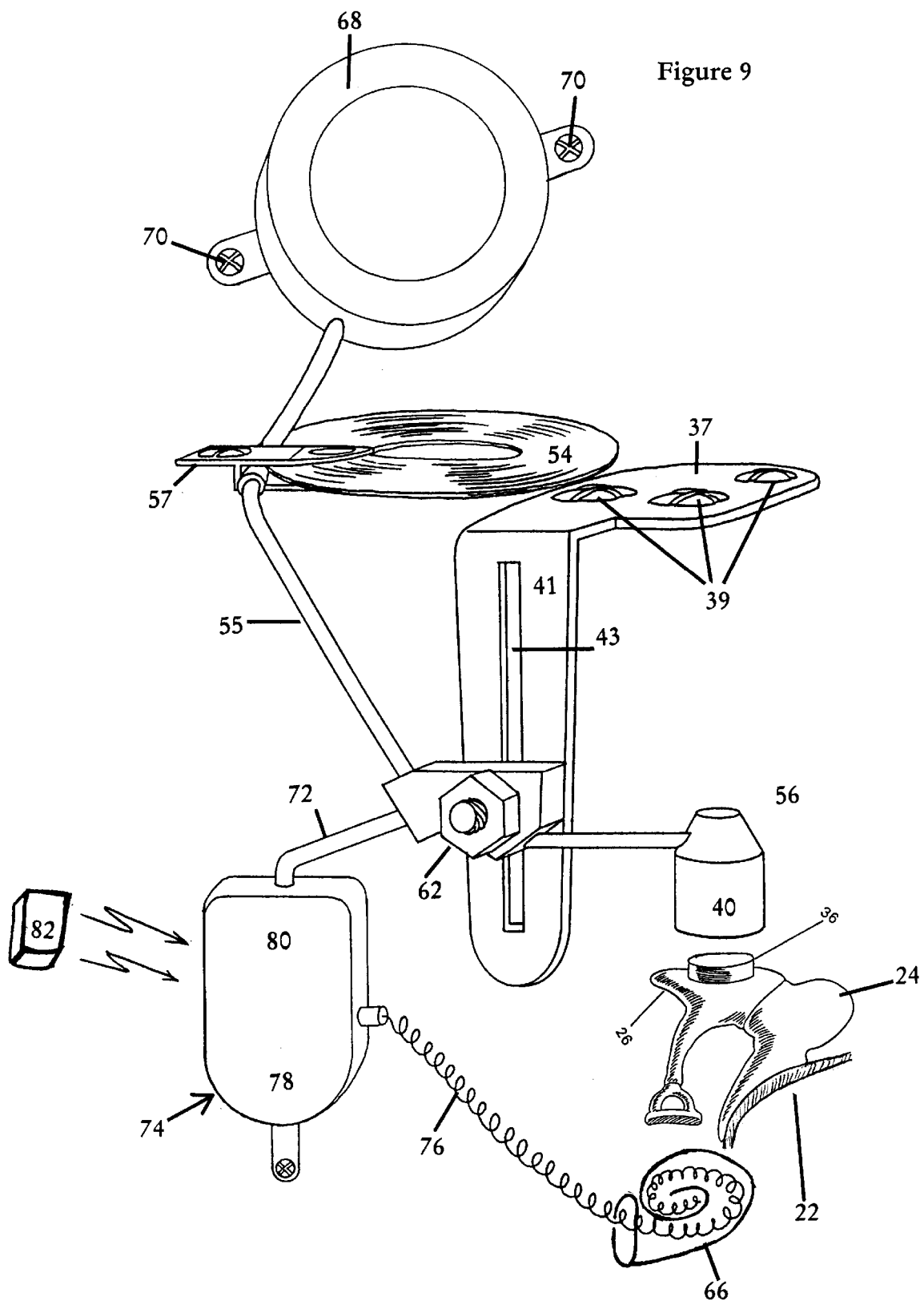
FIG. 9. is an expanded view of the support means and receiving antenna of the FIG. 7. depiction.

The partial hearing loss restoration device is modified as follows to provide a total hearing loss restoration device. Otherwise, the operation and structure thereof remains as described earlier. A battery 68 such as a hermetically sealed rechargeable pacemaker battery is subcutaneously mounted by screws extending through tabs 70 in a known manner. The battery is electrically connected to the titanium tube 55 through a connecting tube 72 of similar construction to power a speech processing and volume control circuit assembly 74 located in the mastoid cavity of the ear. The assembly 74 is hermetically sealed with biocompatible ceramic material contained in a titanium frame and electrically connected to the driver 40 and electronics 56 to receive signals therefrom along connecting tube 72. The assembly 74 has an intracochlear glass insulated feedthrough connecting electrode 76 extending therefrom into the cochlea 66 through the round window of the cochlea to activate the nerve endings of the cochlea as best seen in FIG. 8.

The operation of this device is as follows. The ossicular chain transmits sound and speech signals from the vibration of eardrum 22 which are picked up by the electromagnetic driver 40 due to the changes in the gap d between itself and the magnet 36. These signals are sent to the speech processing and volume control assembly 74 where they are translated into signals which can be processed by the brain. These signals are sent along the intracochlear electrode 76 to the nerve endings of the cochlea 66 to be transmitted by them to the brain. Should the ossicular chain be damaged, then the previously described antenna 54 and microphone 42 may be used to provide speech signals to the assembly 74. It will be obvious that the alternate assembly for the driver 40' magnet 36' and electronics 56' seen in FIGS. 5–6 could also be used for the FIGS. 7–9 embodiments.

The ceramic encased, hermetically sealed assembly 74 is comprised of an on/off and volume control 78 which operates a speech processing assembly 80 for these mentioned functions in response to signals from an externally carried remote control 82 activated by the patient. The signal is picked up by antenna 54 and demodulated into audio frequency (AF) by implanted diode and capacitor in case 40. The speech processor 80 and control 78 is readily available from NUCLEUS CORPORATION of Melbourne Australia. Also Clarion Corporation USA and others have similar speech processors which can be miniaturized into microchips. The eardrum and magnet assembly 36 and electromagnetic coil 40 act as a microphone in a reverse cycle as compared with device described for partial hearing loss. The signal reaches the speech processor which activates the cochlear electrode. In cases of total hearing loss this implant technology has no external unit except for the remote control. The implant unit is totally concealed under scalp and skin harboring in the mastoid middle and inner ear. The battery (implanted, rechargeable) provides the necessary power for operation of the different implanted components. Modifications for children with total hearing loss are contained on FIGS. 6 and 6A to allow for temporal bone growth. Again the electromagnetic coil, magnet assembly ossicles and ear drum function is a microphone to pick sound waves which vibrate the intact ear drum.

Figure 10:
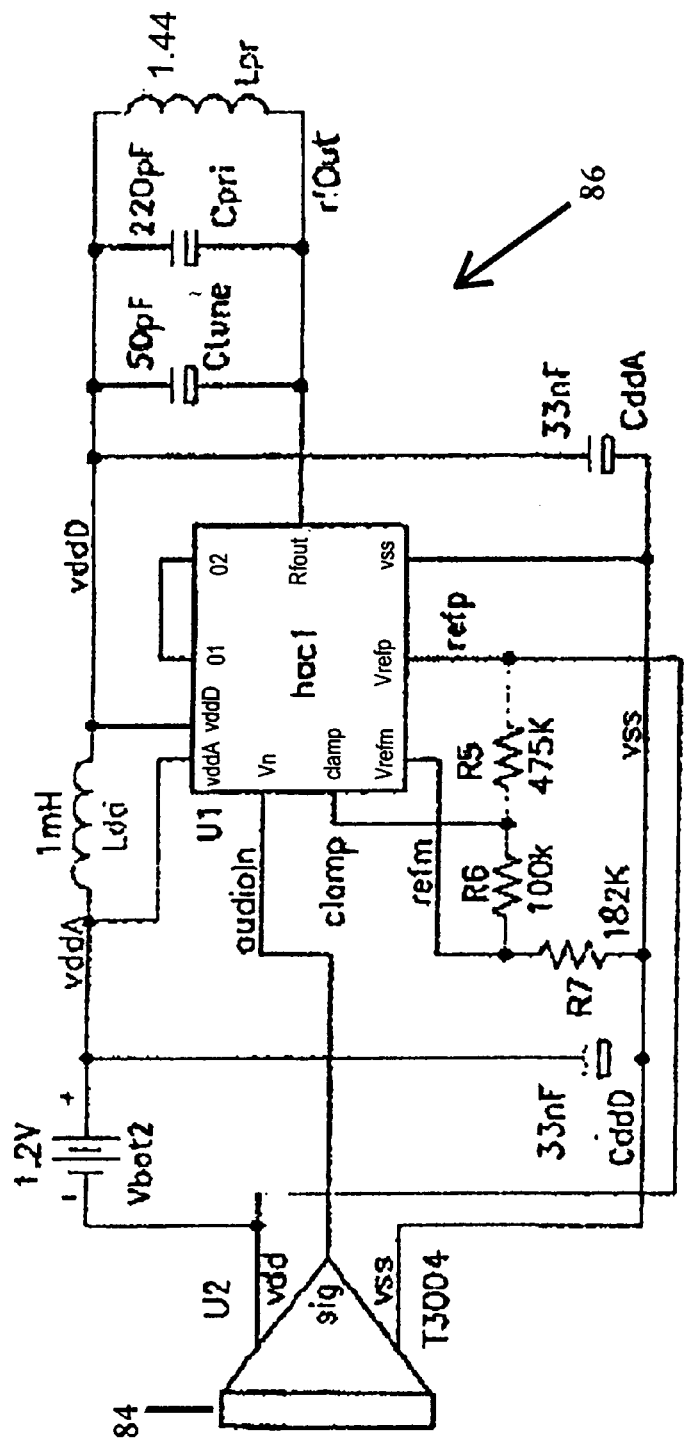
FIG. 10. is an electrical schematic of the external electrical unit of the hearing restoration device of the present invention.

Turning next to FIGS. 10–12, the external unit is shown packaged as a compact unit which is easily located behind the ear 18. This unit is basically a SIEMENS Corporation TRITON hearing aid 86 from rom which the receiver has been removed and coupled to a custom made sigma delta modulator 84 found in the electronics 56. The power supply leads are brought out of the hearing aid 86 and coupled with a second battery 88 to provide the 2.4 V required by the hearing aid 86. The switch 82 also deactivates both batteries to turn off the processor 80. An 8–50 pF variable capacitor 90 (Ctune) is used to tune the external antenna 48 (1 pri). The schematic shows o1 connected to o2 to enable the internal oscillator 92.

Certain improvements and modifications will be obvious to people of ordinary skill in the art area. It will be understood that they have been deleted herein for the sake of conciseness and readability but are fully intended to be within the scope of the following claims.

What is claimed is:

1. A totally implantable hearing device adapted for improvement of total hearing loss comprising;
    a high coercivity permanent magnet adapted to be mounted to the ossicular chain of the middle ear;
    an electromagnet assembly encased in titanium and adapted to be mounted in the attic of the middle ear so as to be activated by a titanium encased target magnet connected to the malleus and ear drum;
    means for actuating said electromagnetic assembly in response to sound and speech variations transmitted by the vibrating ear drum; and
    means adapted to be located within the inner ear for actuating the nerve endings of an unresponsive cochlea in response to signals from the actuated electromagnetic assembly with speech processing signals capable of being understood by the brain.

2. A hearing device as set forth in claim 1 wherein said means for actuating said electromagnetic assembly is a hybrid biologic electronic microphone.

3. A hearing device as set forth in claim 2 wherein said permanent magnet is bonded by a biologically compatible adhesive to the middle ear of the ossicular chain.

4. A hearing device as set forth in claim 1 wherein said actuating means includes a programming microchip system, having a microchip speech processor, a microchip on and off switch and a volume control adapted to be mounted within the mastoid cavity with the on and off switch and programing volume control being actuated by an externally located remote control which transmits by radio frequency electronic signals to an implanted antenna.

5. A hearing device as set forth in claim 4 including a pacemaker type rechargeable battery for actuating said implantable electronics, electromagnetic speech processor adapted to be subcutaneously mounted proximate the ear under the scalp.

6. A hearing device as set forth in claim 1 wherein said means for actuating said electromagnetic assembly includes a sigma delta modulator for radio frequency transmission.

7. A totally implantable hearing device adapted for improvement of total hearing loss due to an unresponsive cochlea comprising;
    programing and speech processing means adapted to be located within the mastoid cavity for receiving signals from the ossicular chain and establishing signals capable of being understood by the brain;
    a coiled electrode adapted to be inserted into the turns of the cochlea proximate the nerve endings thereof for sending the signals from the speech processor means thereto; and
    control means for actuating said programing and speech processing unit to send signals along said intracochlear electrode.

8. A hearing device as set forth in claim 7 wherein said control device means includes an on/off, volume control, and a programmable system actuated by a remote control.

9. A hearing device as set forth in claim 7 including:
    a high coercivity permanent magnet adapted to be mounted to the ossicular chain of the middle ear;
    an electromagnetic assembly adapted to be spacedly mounted within the ear a predetermined distance from said permanent magnet;
    means for actuating said electromagnetic assembly in response to sound speech variations; and
    means for sending the signals from said electromagnetic assembly to said speech processing unit means.

10. A hearing device as set forth in claim 9 including a pacemaker type rechargeable battery for actuating said implanted electronics programing system and speech processor adapted to be subcutaneously mounted proximate the ear.

11. A hearing device as set forth in claim 7 including implanted electronics in the mastoid cavity including microchips for an on/off switch, a volume control, and a programming and speech processor encased in a ceramic box with a titanium frame and feedthrough.

12. A hearing device as set forth in claim 11 including an electromagnetic coil-target magnet assembly spaced by soft silicone rubber and totally contained in a single hermetically sealed titanium case with a glass insulated feedthrough connected to a coiled platinum iridium silicone insulated wire; said assembly adapted to be cemented to the incus by biologically compatible adhesive.

13. A hearing device as set forth in claim 12 wherein said electromagnetic assembly is a biologic-electronic micro phone which transform acoustic energy from ear drum vibration into an electrical signal by an electro magnetic system.

14. A hearing device as set forth in claim 13 wherein said assembly is adapted to be powered by an implantable heart pace maker type battery and with said programing and speech processor microchip adapted to be implanted in the mastoid cavity connected to a coiled wire which activates the cochlear nerve endings, said assembly further including implantable electronics, diodes, capacitors and an implantable and internal antenna adapted to be to be remotely controlled by an external unit having an on/off switch, volume control, and programing capability of a speech processor.

15. A hearing device as set forth in claim 14 including a biologic-electronic microphone to transform acoustic energy produced by eardrum vibration into an electrical signal by means of an electromagnetic system to be used in a totally implantable cochlear implant.

* * * * *